United States Patent [19]

Kliesch

[11] Patent Number: 4,924,707
[45] Date of Patent: May 15, 1990

[54] METHOD OF AND DEVICE FOR COUPLING AN ULTRASONIC PROBE TO A TEST PIECE

[75] Inventor: Wilfried Kliesch, Hagen, Fed. Rep. of Germany

[73] Assignee: Hoesch Aktiengesellschaft, Dortmund, Fed. Rep. of Germany

[21] Appl. No.: 226,756

[22] Filed: Aug. 1, 1988

[30] Foreign Application Priority Data

Aug. 3, 1987 [DE] Fed. Rep. of Germany ....... 3725658

[51] Int. Cl.$^5$ ............................................ G01N 29/04
[52] U.S. Cl. .................................................... 73/644
[58] Field of Search ........................................... 73/644

[56] References Cited

U.S. PATENT DOCUMENTS

| | | | |
|---|---|---|---|
| 3,159,756 | 12/1964 | Beaujard et al. | 73/644 |
| 3,303,691 | 2/1967 | Beaujard et al. | 73/644 |
| 3,420,097 | 1/1969 | Batterman et al. | 73/644 |
| 3,631,714 | 1/1972 | Cressman et al. | 73/644 |
| 3,745,833 | 7/1973 | Armstrong | 73/644 |
| 4,351,190 | 9/1982 | Rehme et al. | 73/638 |

FOREIGN PATENT DOCUMENTS 1568857  5/1969  France ................................. 73/638

*Primary Examiner*—Michael J. Tokar
*Assistant Examiner*—Mark A. Spector
*Attorney, Agent, or Firm*—Max Fogiel

[57] ABSTRACT

An arrangement in which at least one ultrasonic sensor is coupled to an article to be tested by a liquid coupling medium in an automatic ultrasonic testing of strips, sheets, and pipes that follow each other as individual pieces. The sensor is positioned along a testing path at a constant distance away from the article by a holder. The sensor has a sound emisson surface, and at least one separate free jet of coupling medium is positioned at a side of the sensor in a plane crossing the testing path. The free jet intercepts a central axis of the sound emission surface, and a layer of coupling medium is formed between the sound emission surface and the surface of the article. Testing of the article includes interior regions covered by all surfaces of the article, as well as the end regions and edges of the article.

13 Claims, 3 Drawing Sheets

METHOD OF AND DEVICE FOR COUPLING AN ULTRASONIC PROBE TO A TEST PIECE

There are many methods at the state of the art that employ a liquid coupling medium to directly couple sensors or oscillators that emit ultrasonic vibrations to a workpiece that is to be tested.

One group consists of methods that employ a free jet emerging from a nozzle and either communicating— prior to its existence as an actual free jet, before emerging from the nozzle, that is—with the ultrasonic sensor or oscillator or washing over it and acting as a "sound channel" after emerging from the nozzle.

To prevent reflections against the free surface of the jet, the sound in the jet must travel parallel to the axis of the jet. The flow of the jet employed in the free-jet technology is also laminarized to prevent the reflections that may occur as the result of variations in the density of a turbulent jet.

These peculiarities on the part of a free jet result in the drawback that the sound always enters perpendicular to the surface of the piece being tested. Introducing the sound at a non-perpendicular angle is possible. However, free jets that are aimed at a non-perpendicular angle to the surface of the piece are unstable in terms of coupling, only with methods that produce the angle by way of many parallel free jets and exploit a variable phased array on the part of the oscillator. Methods of this type, like that described for example in German OS No. 2 926 933, entail the drawback of a very wide jet cone, are complicated due to the many oscillators involved, and are not appropriate for testing thin walls.

Thus, the conventional perpendicular-jet coupling method can admittedly be employed to measure wall thickness or to test for concavities and overlaps in the material that are relatively parallel to the surface.

Free-jet couplings of the known type cannot be employed to test welding seams in longitudinally welded pipes for example.

The other group of methods consists of those that operate in conjunction with what is called a water chamber. The sensor, of the type illustrated in FIG. 5 of German Patent No. 971 832, is accommodated in a water chamber that is open toward the piece being tested and has a water-supply line. The water is removed either through gaps between the chamber and the surface of the piece and/or through water outlets in the chamber.

One drawback to this system is the air bubbles that always occur in the chamber when the water pressure is not high enough and lead to undesired reflections.

Another and essentially more serious drawback is that it takes a long time to establish stable testing conditions because, once the chamber has been applied to the surface of the piece, it must be filled with water, the air bubbles must be removed from it by circulation or otherwise, and it must be set in motion. Given the rapidity with which automatic testing is now being conducted, accordingly, an untested or insufficiently tested section will remain at the beginning and end of every pipe—in the example of testing welding seams for instance—while stable testing conditions are being established and disestablished respectively. These sections must then be tested manually, which prolongs the process considerably.

Another drawback of a water chamber is that, even when the surface of the piece is only slightly irregular, the gap between the chamber and the piece can be large enough for the chamber to leak or suction in air, and the results will not be reliable. This is especially true of larger chambers that employ several sensors.

The object of the invention is accordingly to provide a method of coupling that will ensure stable coupling of the sensors in automatic piece-by-piece testing at a rapid rate, that will allow any angle of sound incidence, that will be insensitive to irregularities in the surface, and that will accordingly eliminate the need for manual follow-up testing.

This object is attained by way of the characteristics recited in the body of claim 1.

Further characteristics are recited in the subsidiary claims.

Also disclosed is a device appropriate for carrying out the method in accordance with the invention.

The layer of coupling medium between the sound-emission surface and the surface of the piece being tested is in a practical way created by means of a separate free jet at the side of the sensor that does not in itself act as a sound channel. This free jet, accordingly, does not need to be laminarized or to communicate with the sensor through complicated flow channels. The jet extends in a plane that crosses the testing trace, includes the central axis of the sensor's sound-emission surface, and is oriented toward the gap between the sound-emission surface and the surface of the test piece in the testing state. Structure and orientation are dictated by a free-jet generator that slopes toward the sensor.

The advantage of a free jet of this type is that a constant layer of coupling medium is established in the gap between the sound-emission surface and the surface of the test piece by the time the initial section of the piece arrives at the center of the sound-emission surface and that the layer remains in existence until the terminal section of the piece arrives at the center of the sound-emission surface.

The sound-emission surface of the sensor is slightly elevated in relation to the bottom of a holder that faces the test piece. The sound-emission surface and the surface of the test piece accordingly demarcate the shortest distance, with the exception of the rollers, between any component of the testing apparatus and any component of the test piece.

Thus there is no chamber around the sound-emission surface, but only two essentially parallel surfaces that, as soon as a free jet of usually adhesive coupling medium is directed between them from the side, convert it into a gap flow while completely wetting the sound-emission surface and the facing and equally large surface of the test piece.

The sound will now penetrate at an angle to the direction of propagation of the free jet, which has been converted into a gap flow, allowing the sound to enter at any angle. The adhesive forces at the opposite surfaces immediately result in a gap that is completely full and contains no bubbles and hence in stable testing conditions.

When, as when testing a sheet of metal that has a welded seam, the surface of the test piece and the sound-emission surface are basically not parallel, it is practical to aim the free jet in the vicinity of and adjacent to the gap demarcated by the surfaces, against the surface of the test piece for example, which will accordingly assume the function of channeling the jet. This embodiment of the method in accordance with the invention is especially practical in testing longitudinal welded seams in pipes, in which case the free jet will be aimed at the surface of the test piece in the immediate vicinity of the sound-emission surface. In this case the sound-emission surface will not get wet in the absence of a test piece, which would lead to a contaminating water echo. It is accordingly no longer necessary to discontinue testing during the intervals between individual pieces.

The coupling medium in one especially practical embodiment of the invention is outside the gap, is either a free jet or flows freely over the surface of the test piece, and is defined, channeled, or divided into subsidiary flows by means of jets of air. This procedure can occur either at the free jet, around the layer that has built up in the gap, or during free flow-off, and one of its purposes is to keep specific points where the ultrasonic beam reflects against the wall of the material inside the test piece free of water and prevent uncoupling and double reflections. Another purpose is to ensure separation of the coupling medium on the part of different and adjacent sensors, another means of avoiding errors. Several air nozzles are for this purpose positioned in a practical way in the vicinity of the sensor.

It is in this case helpful to aim the free jet at the surface of the test piece at as acute an angle as possible. This measure not only augments the conductivity of the surface and accordingly accelerates the flow of the coupling medium out of the testing area, but also does not demand as much pressure in the air-jet components that promote the outflow.

The angle between the axis of the free jet and that of the sensor is preferably between 40° and 90°.

This measure is accomplished by means of appropriately angling and orienting the component that generates the free jet.

When several adjacent sensors are employed to test for various types of failure, the component that generates the free jet in that particular embodiment of the invention is a slotted nozzle that generates a jet over the total width of the adjacent sensors.

In this case it is practical to section the extended free jet into individual sections, each associated with one sensor, by means of jets of air in order to prevent undesired coupling and reflection.

The invention will now be specified with reference to one embodiment in the form of a coupling device for the ultrasonic testing of longitudinal welding seams in pipes.

Figure 1:
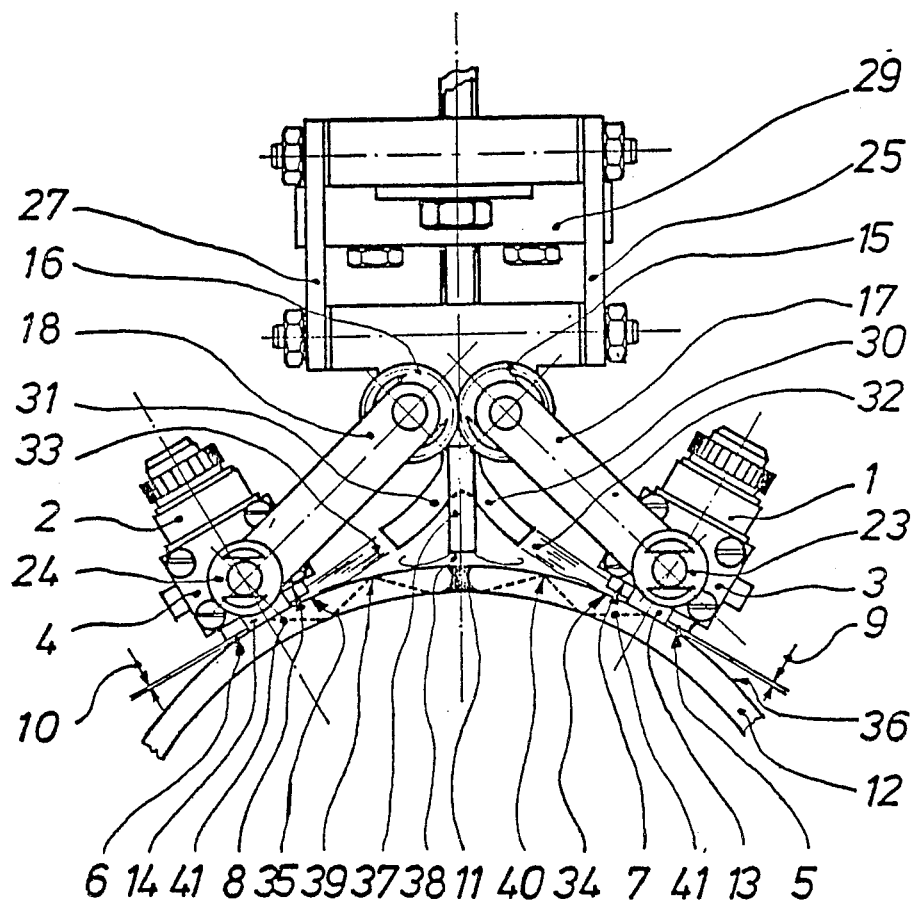
FIG. 1 is a front view of a coupling device in accordance with the invention.
Figure 2:
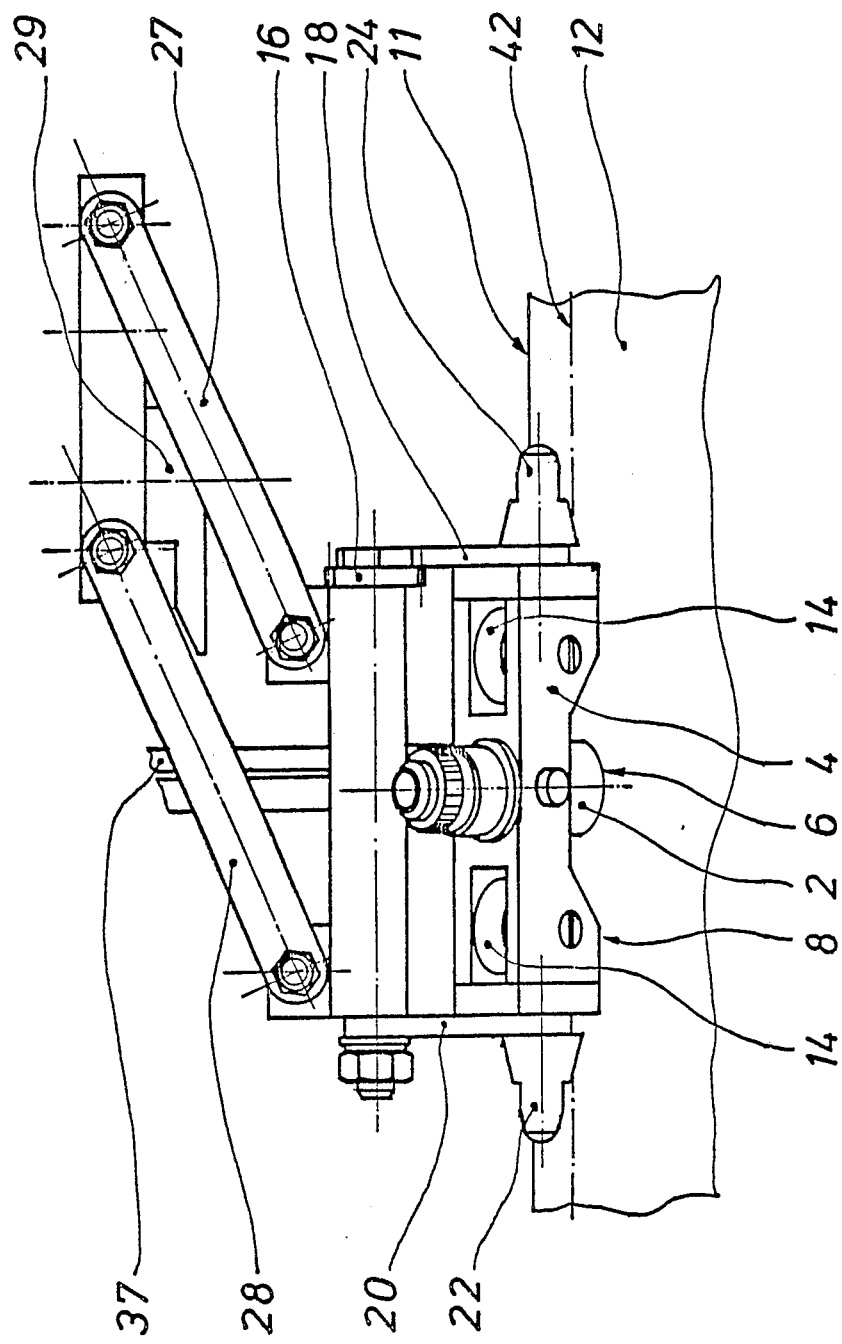
FIG. 2 is a side view of the device.

FIGS. 1 and 2 show two sensors 1 and 2 in holders in the form of roller carriages 3 and with their sound-emission surfaces 5 and 6 elevated relation to the bottoms 7 and 8 of the holders. Sound surfaces 5 and 6 are accordingly distances 9 and 10 away from the piece being tested.

The components are employed to test the longitudinal welded seam 11 of a pipe 12 for faults along the weld. Carriages 3 and 4 are suspended along with their rollers 13 and 14 on rocking arms 17, 18, 19, and 20 that are synchronized by cogwheels 15 and 16 and adjusted to the diameter of the individual pipe and tightened with screws.

Screwed to the front and rear of each carriage 3 and 4 are skids 21, 22, 23, and 24 that position the carriages, which move up and down on four-point linkages 25, 26, 27, and 28, against the initial section of pipe as it initially enters the testing area and allow them to gradually slide off the terminal section as the pipe leaves. A horizontally adjustable stop 29 limits the vertical swinging motion as a function of the diameter of the pipe.

Free-jet generating components, in the form of tubular nozzles 30 and 31 in the present case, aim free jets 32 and 33 of coupling medium at gaps 34 and 35, coupling the sound-emission surfaces 5 and 6 of sensors 1 and 2 against the surface 36 of the test piece.

An air nozzle 37 directs a jet 38 of air at the surface 36 of the test piece in the vicinity of welded seam 11.

This measure not only avoids undesired coupling between free jets 32 and 33 but also orients the particular jet such that the relevant points 39 and 40 of reflection of sound jet 41 will be outside the wetted surface of the test piece while a testing path 42 is being traveled.

Figure 3:
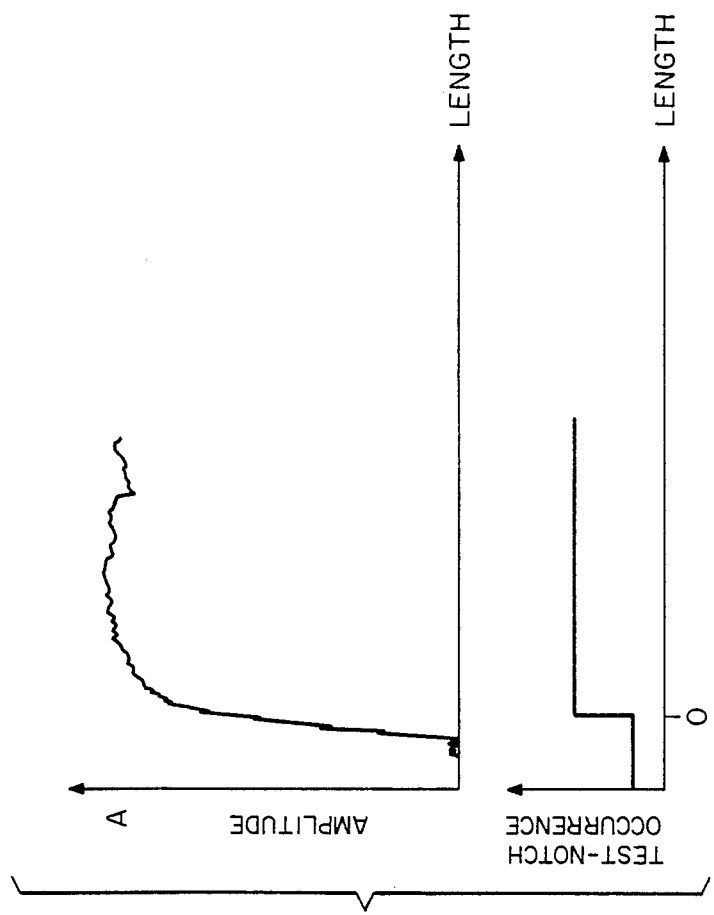
FIG. 3 illustrates the increase in the amplitude of a signal from a 10% interior groove as the coupling device travels over a pipe.

FIG. 3 illustrates the increase in the amplitude A of a 10% interior failure signal as the coupling device travels over the initial section of a pipe of length L. It will be evident that, even before the total sound-emission surface 5 or 6 of a sensor 1 or 2 has traveled overpipe 12, prior, that is, to the point 0 in the lower failure graph, the amplitude is increasing rapidly and accordingly allows constant failure detection even at the initial section of the pipe. No manual retesting of for example the first 25 mm of pipe will accordingly be necessary.

The two sensors 1 and 2 can of course also be employed as send-receive sensors that are constantly interswitched at prescribed intervals as well as sensors with only one function each.

It is also conceivable to test with only one send-receive sensor and only one free-jet generator, switching over to receive once the ultrasonic signal has been emitted and processing the echo signal.

What is claimed is:

1. A method of coupling at least one ultrasonic sensor to an article to be tested by a liquid coupling medium in an automatic ultrasonic testing of strips, sheets, and pipes following each other as individual pieces, testing of said article including interior regions covered by all surfaces of said article as well as end regions and edges of said article, said method comprising the steps of: positioning said sensor along a testing path at a constant distance away from said article by a holder, said sensor having a sound emission surface with a central axis, said central axis being an axis of symmetry of said sound emission surface; positioning at least one separate free jet of coupling medium at a side of said sensor, said free jet having an axis of symmetry lying in a plane crossing said testing path, said free jet being free of exterior confining surfaces; said axis of said free jet intercepting said central axis of said sound emission surface; and forming a layer of coupling medium between said sound emission surface and the surface of said article by said jet.

2. A method as defined in claim 1, and further demarcating at least two free jets by at least one jet of air for preventing transmission of ultrasonic signals from one free jet to the other free jet through said coupling medium and preventing coupling medium to be applied over regions in which reflections of said ultrasonic signals occur.

3. A method as defined in claim 1, and further defining and demarcating said free jet by at least one jet of air.

4. A method as defined in claim 1, wherein said free jet and said sensor have central axes, and generating said free jet sloping at an angle to said sensor so that said central axes of said free jet and said sensor include an angle of between 40° and 90°, said angle having sides intersecting at a point located below said surface of said article.

5. A method as defined in claim 1, and further demarcating a layer of coupling medium by at least one jet of air.

6. A method as defined in claim 1, and further aiming said free jet at a surface of said article to be tested in vicinity of a gap demarcated by said sound emission surface and said surface of said article.

7. A method as defined in claim 6, wherein said free jet is aimed at an acute angle to said surface of said article to be tested.

8. An arrangement for coupling at least one ultrasonic sensor to an article to be tested by a liquid coupling medium in an automatic ultrasonic testing of welded seams in pipes following each other as individual pieces, testing of said article including interior regions covered by all surfaces of said article as well as end regions and edges of said article, said arrangement comprising: holding means for mounting said sensor and positioned along a testing path at a constant distance away from said article; rocker arm means and four-point linkage means for raising and lowering said holding means and adjusting to the dimensions of the pipes; said rocker arm means and four-point linkage means having means fixed to said sensor for moving over said pipes by rolling without tipping; said sensor having a sound emission surface with a central axis above said holding means facing the surface of said article, said central axis being an axis of symmetry of said sound emission surface; means for generating a free jet of coupling medium positioned at a side of said sensor, said free jet being free of exterior confining surfaces; said means for generating said free jet being separated from said sensor and being at an angle to said sensor; said jet having an axis of symmetry emerging across said testing path in a plane containing the central axis of said sound emission surface, said plane containing said axis of said jet and said axis of said sound emission surface; said axis of said jet being aimed substantially at a gap between said sound emission surface and the surface of said article to be tested.

9. An arrangement as defined in claim 8, wherein said means for generating said free jet comprises a slotted nozzle.

10. An arrangement as defined in claim 8, including means for generating a jet of air at a layer of coupling medium in vicinity of said sensor.

11. An arrangement as defined in claim 8, including means for generating a jet of air aimed at said surface of said article in vicinity of said sensor.

12. An arrangement as defined in claim 8, including means for generating a jet of air aimed at at least two free jets in vicinity of said sensor for preventing transmission of ultrasonic signals from one free jet to the other free jet through said coupling medium and preventing coupling medium to be applied over regions in which reflections of said ultrasonic signals occur.

13. An arrangement for coupling at least one ultrasonic sensor to an article to be tested by a liquid coupling medium in an automatic ultrasonic testing of welded seams in pipes following each other as individual pieces, testing of said article including interior regions covered by all surfaces of said article as well as end regions and edges of said article, said arrangement comprising: holding means for mounting said sensor and positioned along a testing path at a constant distance away from said article; rocker arm means and four-point linkage means for raising and lowering said holding means and adjusting to the dimensions of the pipes; said rocker arm means and four-point linkage means having means fixed at said sensor for moving over said pipes by rolling without tipping; said sensor having a sound emission surface with a central axis above said holding means facing the surface of said article, said central axis being an axis of symmetry of said sound emission surface; means for generating a free jet of coupling medium positioned at a side of said sensor, said free jet being free of exterior confining surfaces; said means for generating said free jet separated from said sensor and being at an angle to said sensor; said jet having an axis of symmetry emerging across said testing path in a plane containing the central axis of said sound emission surface, said plane containing said axis of said jet and said axis of said sound emission surface; said axis of said jet being aimed substantially at a gap between said sound emission surface and the surface of said article to be tested; said sensor having an axis of symmetry, said means for generating said free jet sloping at an angle to said sensor so that the axes of said free jet and said sensor include an angle of between 40° and 90°, said angle having sides intersecting at a point located below said surface of said article.

* * * * *